(12) United States Patent
Zerfas et al.

(10) Patent No.: US 10,470,820 B2
(45) Date of Patent: Nov. 12, 2019

(54) LASER OPTICAL FIBER FOR ENDOSCOPIC SURGICAL PROCEDURES HAVING A RE-COATED ELONGATED TIP WITH VISUAL BURN-BACK INDICATOR AND AN IMPROVED SELF-ALIGNING STABILITY SHEATH

(71) Applicants: Jeffrey W. Zerfas, Bloomington, IN (US); Alfred P. Intoccia, Jr., Nashua, NH (US)

(72) Inventors: Jeffrey W. Zerfas, Bloomington, IN (US); Alfred P. Intoccia, Jr., Nashua, NH (US)

( * ) Notice: Subject to any disclaimer, the term of this patent is extended or adjusted under 35 U.S.C. 154(b) by 523 days.

(21) Appl. No.: 15/275,320

(22) Filed: Sep. 23, 2016

(65) Prior Publication Data

US 2017/0079716 A1   Mar. 23, 2017

Related U.S. Application Data

(60) Provisional application No. 62/222,285, filed on Sep. 23, 2015.

(51) Int. Cl.
*A61B 18/22* (2006.01)

(52) U.S. Cl.
CPC ...... *A61B 18/22* (2013.01); *A61B 2018/2222* (2013.01); *A61B 2018/2233* (2013.01); *A61B 2018/2244* (2013.01)

(58) Field of Classification Search
CPC ............................................. A61B 2018/2244
See application file for complete search history.

(56) References Cited

U.S. PATENT DOCUMENTS

| | | | | |
|---|---|---|---|---|
| 6,190,303 B1* | 2/2001 | Glenn | ..................... | G21F 5/018 600/1 |
| 6,361,530 B1* | 3/2002 | Mersch | ................... | A61B 18/22 264/1.24 |
| 6,493,575 B1* | 12/2002 | Kesten | ................... | A61B 90/36 600/431 |
| 8,574,258 B2* | 11/2013 | Braun | ............... | A61B 17/12022 606/198 |
| 2011/0318701 A1* | 12/2011 | Nakatate | .............. | A61C 1/0046 433/29 |

* cited by examiner

*Primary Examiner* — Scott Luan
(74) *Attorney, Agent, or Firm* — Russ Weinzimmer & Associates, P.C.

(57) ABSTRACT

A laser fiber, is modified to have a tip that has a length that is predetermined to ensure that the tip remains viable throughout a given procedure type, despite the presence of burn-back. The extended tip is defined by stripping back the jacket of the laser fiber over the pre-determined length starting at the distal end of the fiber. The stripped portion of the fiber is then dip-coated with a layer of polymeric coating such as an acrylate. A visual indicator can be printed onto the extended tip to aid in the use of the extended fiber. A self-aligning stability sheath is provided to make insertion easier in certain types of endoscopes. The laser fiber with extended tip can be pre-inserted into the sheath and sold as a pre-prepared kit for ease of use and protection of the fiber.

17 Claims, 6 Drawing Sheets

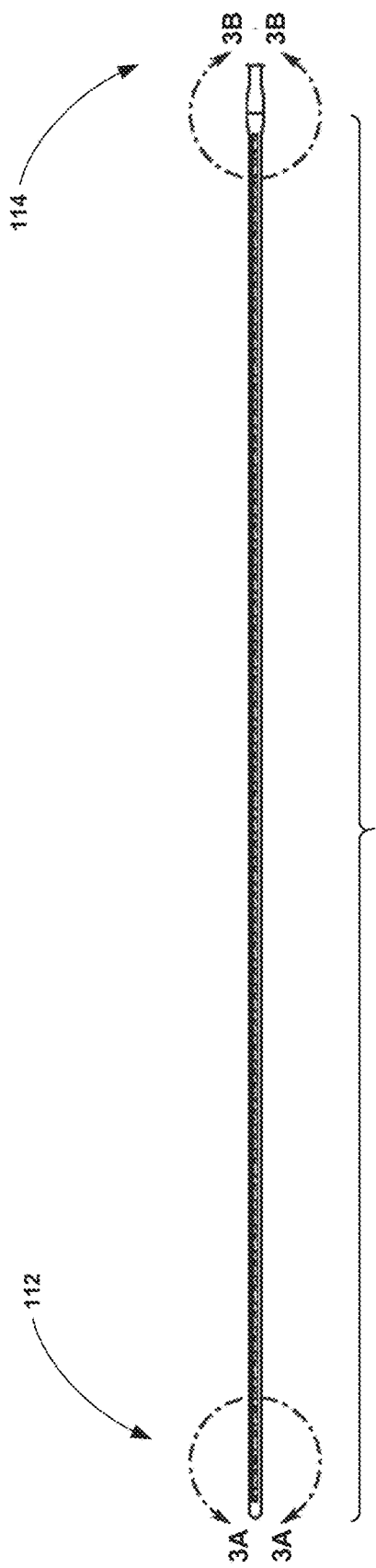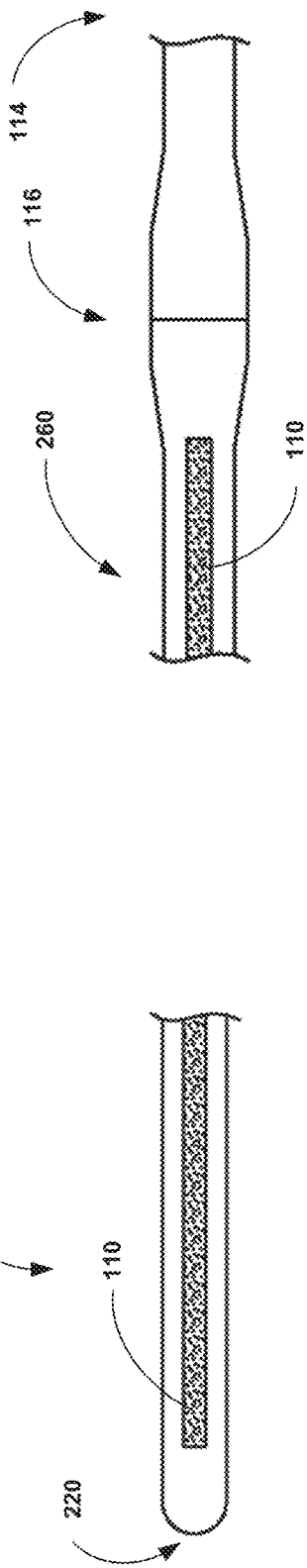

LASER OPTICAL FIBER FOR ENDOSCOPIC SURGICAL PROCEDURES HAVING A RE-COATED ELONGATED TIP WITH VISUAL BURN-BACK INDICATOR AND AN IMPROVED SELF-ALIGNING STABILITY SHEATH

CROSS-REFRENCE TO RELATED APPLICATION

This application claims priority to U.S. Provisional Application Ser. No. 62/222,285 filed Sep. 23, 2015 and entitled "OPTICAL FIBER AND STABILITY SHEATH FOR MINIMALLY INVASIVE SURGICAL PROCEDURE," and which is incorporated herein in its entirety by this reference.

FIELD OF THE INVENTION

This disclosure relates generally to endoscopic medical devices, and more specifically to endoscopic devices employing optical fibers through which laser energy is delivered to a surgical field.

BACKGROUND OF THE INVENTION

An endoscopic procedure is a minimally invasive surgical technique where an endoscope is inserted into the body through a small incision or body opening. In general, endoscopic procedures tend to produce shorter recovery times, a reduced risk of infection, and reduced scarring as compared with conventional surgical techniques. However, endoscopic procedures also often require greater precision and skill of the personnel who actually perform the procedure.

A typical endoscope includes an optical system capable of imaging the surgical field. Some endoscopes include a utility lumen (a tube-like channel) through which a wide range of diagnostic and/or treatment devices can be passed, including optical laser fibers. Some endoscopes, such as cystoscopes, provide little in the way of stability features through which the fiber is disposed and supported, and thus require an additional stability element to be supplied with the fiber.

Many currently employed endoscopic surgical procedures involve delivering laser energy to a surgical field through an endoscope for the purpose of, for example, making an incision, fragmenting kidney stones or removing tissue. Holmium laser enucleation of the prostate (HoLEP) is one such procedure, which is used to treat benign prostatic hyperplasia (BPH) by removing tissue from the prostate. Laser lithotripsy, used to fragment kidney stones, is another. In both of these examples, an optical fiber, which is disposed through the endoscope, is used to deliver energy generated by an externally-positioned laser to the treatment site within the patient's body.

The optical fiber commonly used to deliver the laser energy in procedures such as lithotripsy and HoLEP is known in the art as a "straight fire" laser fiber. The laser fiber is typically comprised of a series of layers, including: a) an optical "core" most commonly made of silica; b) a "clad" (sometimes referred to as the primary clad) that covers the core and is typically made up of a fluorinated silica; c) a clear "coating" (sometimes referred to as the secondary clad) that covers the primary clad and is typically made of a low index acrylate; and d) a jacket that covers and protects the coating or secondary clad, typically comprised of ethylene tetrafluoroethylene (ETFE). The diameter of the core for these fibers can typically range from 150 to 1,000 microns.

During an ureteroscopy procedure (e.g. lithotripsy), a medical practitioner can insert an ureteroscope into a patient's urinary tract, for example, over a guide wire to locate an undesirable object such as a kidney stone or a bladder stone. Once the stone is located, an optical fiber can be introduced into the utility lumen (i.e. working channel) of the ureteroscope and advanced until a portion of the distal end of the optical fiber, called a tip, comes into contact with or in close proximity to the stone. A red or green aiming beam is emitted from the tip of the optical fiber to target the object. Electromagnetic radiation from, for example, a holmium (Ho) laser can also be directed through the optical fiber towards the stone to break the stone into fragments. The fragments can then be removed with a retrieval device via the working channel or flushed through normal urinary activity.

Ureteroscopes generally have an outside diameter of approximately 9 French and have a very small working channel, which requires a small optical fiber (typically having a core diameter in the range of 150 to 365 microns). The smaller the fiber diameter, the more fragile is the fiber. Many known optical fibers that are used in ureteroscopy procedures are supplied by manufacturers with approximately 4 mm of the jacket and coating stripped off of the distal end, thereby exposing the silica core and clad (this area forms the tip). The coating layer, which is necessary to protect the core and clad, is partially or completely removed when the Jacket is stripped off. Therefore, the tip is susceptible to damage and moisture degradation, which is the reason manufacturers tend to limit the stripped length to approximately 4 mm.

During use, the hard silica core and fluorinated silica clad forming the tip slowly chips away until the 4 mm tip is completely gone (this process is known as burn-back). The core, clad and coating are translucent, which can be difficult for the operator to see when firing the laser. However, the jacket is opaque, making it easy to view during use. This is another reason why manufacturers limit the length of their tips to 4 mm. This length ensures that the proximate end of the tip, which ends where the jacket has not been removed, provides the operator a reference regarding the remaining length of the tip. Once the tip is consumed, continued use eventually causes the jacket to fray, thus impeding the ability to aim the laser. Therefore, if the fiber burns back to the jacket during, and prior to completion of, a procedure, the procedure must be delayed while the fiber is removed from the ureteroscope, an additional 4 mm of jacket is stripped off and the fiber is reinserted through the working channel of the ureteroscope to continue the procedure.

Thus, medical personnel must not only be skilled in the use of the endoscope and the laser fiber in performing the surgical procedure, but they must also be able handle removal of the fiber from the endoscope, stripping of the jacket layer to create a new tip, and then the re-installation of the fiber into the endoscope, all without damaging or compromising the efficacy of the fiber so that the procedure may be ultimately completed successfully. This is not a simple task, as the OD (outside diameter) of the fibers is very small, so the glass fibers are delicate and the jacket layer is thin.

HoLEP procedures typically require a core optical fiber having a diameter of 550 microns. In this procedure, the fiber is passed through a stability sheath that is secured inside a cystoscope with a 24 or 26 French outside diameter.

Burn-back of the fiber's tip occurs at an even faster rate during HoLEP procedures. To remove prostate tissue, the laser is operated at much higher energy (about 100 watts) and for a longer duration relative to other procedures. Thus, to accommodate the increased burn-back during the procedure, this procedure requires a substantially longer (i.e. up to 10 cm) tip than the 4 mm tip typically provided by the manufacturer. As a result, medical personnel must first strip off approximately 10 cm of the jacket just prior to initiating the procedure. This is sometimes difficult to do in an OR setting and often results in broken tips and delays. Stripping an optical fiber just prior to use also requires the use of a sterile fiber optic stripper, which a hospital may not have.

After removing the Jacket, the fiber is inserted into a stability sheath which is used to guide the laser fiber through the scope and to the target. This because the cystoscope does not include a utility lumen through to pass the fiber. Typical stability sheaths are over 30 cm in length, having an outside diameter of approximately 7.5 French with a blunt tip. Prior to inserting the cystoscope into the patient, the stability sheath is inserted through an elastomeric seal at the proximal end of the cystoscope and is pushed through a positioning ring located inside the distal end of the cystoscope. The inside diameter of the locating or positioning ring is approximately 8 French.

The medical practitioner guides the stability sheath through the positioning ring until the distal end of the stability sheath is flush with the distal end of the scope. Maintaining this flush position can be difficult while advancing the fiber to the target. Often, misalignment of the stability sheath with the ring during insertion occurs, because there is no line of sight during the insertion. This misalignment leads to the stability sheath butting up against the proximal end of the positioning ring making it difficult to feed through the ring. The cystoscope is comprised of 2 main parts, the camera and the optical system that is inserted into an outer tube (or cannula) and locked into place. It is common for medical personnel to briefly separate the optical portion of the scope from the scope cannula to visualize the distal end of the stability sheath, to aid in aligning the sheath as it is pushed through the scope cannula and into the positioning ring.

In summary, there are a number of reasons that manufacturers of laser fibers limit the length of the tips provided therewith to about 4 mm. First, the tips are vulnerable to damage and moisture compromise prior to use. The longer the tips, the greater is that vulnerability. In addition, tips that extend longer than about 4 mm will force the line where the jacket begins (at the distal end of the tip) to be outside of the surgical view, making it harder to gauge how far the tip extends from the end of the scope as its length is consumed by burn-back. Yet, certain procedures require tips significantly longer than 4 mm standard size to be completed without interruption. Moreover, it requires medical personnel to be skilled enough to strip the jacket layer to establish a new tip, either during a procedure where the tip has been completely consumed back to the jacket, or prior to commencing the procedure because it is known that a much longer tip length will be required before the procedure is even initiated.

Laser Fibers that require a stability sheath for support within certain endoscopes are often difficult to insert into a guide feature or ring, and further require that alignment with the end of the scope be performed manually by the operator performing the procedure.

SUMMARY OF THE INVENTION

In one aspect of the invention, an embodiment includes a laser fiber for delivering laser energy to a surgical field during at least one type of endoscopic surgical procedure. The laser fiber has an elongate silica core having a proximal and distal end, the proximal end of which is configured to be coupled to a laser. The laser fiber further includes a layer of silica cladding material surrounding the core, an original layer of polymeric coating surrounding the silica cladding, and then a fluoropolymer jacket surrounding the original polymeric coating. The laser further includes a tip that extends from a distal end of the fiber and has a predetermined length. The tip of the fiber is defined by completely stripping the jacket from the laser fiber over the length of the tip, and then applying a second polymeric coating over at least the length of the tip. The predetermined length ensures that at least a portion of the tip will remain continuously viable, notwithstanding burn-back of the tip, throughout the at least one type of surgical procedure.

In an embodiment of the laser fiber, a visual indicator is printed substantially over the length of the tip.

In an embodiment of the laser fiber of the invention, at least the second polymeric coating is an acrylate.

In another embodiment of the laser fiber of the invention, the predetermined length is at least one centimeter.

In still another embodiment of the laser fiber of the invention, the fluoropolymer jacket material is tetrafluoroethylene (ETFE).

In a further embodiment of the laser fiber of the invention, the second polymeric coating at least partially overlaps the fluoropolymer jacket.

In yet another embodiment of the laser fiber of the invention, the length of the tip is between about 1 centimeter and about 15 centimeters.

In another aspect of the laser fiber of the invention, the laser fiber is prepared by a process that includes.

In another aspect of the invention, the laser fiber of the invention delivers laser energy to a surgical field continuously for the duration of at least one type of endoscopic surgical procedure, and the laser fiber is prepared by a process that includes providing a laser fiber that includes an elongate silica core having a proximal and distal end, the proximal end configured to be coupled to a laser, a layer of silica cladding material surrounding the core, an original layer of polymeric coating surrounding the silica cladding, and a fluoropolymer jacket surrounding the polymeric coating. A tip for the fiber is then formed that extends from the distal end of the laser fiber for a predetermined length. The tip is formed by stripping the jacket completely from the laser fiber over the length of the tip, and then applying a second polymeric coating over at least the length of the tip. The predetermined length ensures that at least a portion of the tip will remain continuously viable, notwithstanding burn-back of the tip, throughout the at least one type of surgical procedure.

In an embodiment, the process further includes applying a visual indicator over at least a portion of the length of the tip.

In another embodiment, second polymeric coating is applied by dipping at least the tip portion of the laser fiber into the polymeric coating.

In a further embodiment, at least the second polymeric coating is an acrylate.

In a still further embodiment, the applying further includes pad printing the visual indicator to the second polymeric coating.

In some embodiments, the predetermined length of the tip portion ranges between about 1 centimeter and about 15 centimeters.

In a still further aspect of the invention, a laser fiber assembly delivers laser energy to a surgical field through an endoscope and includes a laser and a stability sheath. The laser has an elongate silica core having a proximal and distal end, the proximal end configured to be coupled to a laser, a layer of silica cladding material surrounding the core, an original layer of polymeric coating surrounding the silica cladding, a fluoropolymer jacket surrounding the polymeric coating, and a tip that extends from a distal end of the fiber and having a predetermined length. The tip is defined by completely stripping the jacket from the laser fiber over the length of the tip, and applying a second polymeric coating over at least the length of the tip.

The stability sheath includes an elongate hollow polyurethane tube having an inner diameter and an outer diameter, wherein the inner diameter of the tube is large enough to permit the laser fiber to pass therethrough, and the inner and outer diameters of the tube decreasing to form a taper at distal end of the tube. The distal end of the laser fiber is configured to be inserted into the proximate end of the stability sheath, and the proximate end is configured to receive a Tuohy-Borst adapter. When the assembly is inserted into a proximate end of the endoscope, the tapered distal end of the stability sheath is configured to be received by a feature disposed at a distal end of the endoscope, the ring feature having a diameter that is at least less than the outer diameter of the non-tapered portion of the stability sheath such that the tapered distal end of the stability sheath will engage with, but not pass entirely through, the ring feature, thereby self-aligning the sheath with the end of the endoscope.

In an embodiment, the Tuohy-Borst adapter is configured to resist movement of the laser fiber within the stability sheath.

In another embodiment, the stability sheath is made of polyurethane.

In a further embodiment, the tip of the laser fiber includes a visual indicator printed over at least a portion of the length of the tip.

In a still further embodiment, the predetermined length of the tip ranges between about 2 centimeters and about 15 centimeters.

In yet another embodiment, the second polymeric coating extends past the tip portion to form an overlapping portion where the second polymeric coating overlaps the jacket layer.

In another aspect of the invention, the laser fiber of the invention and the self-aligning stability sheath can be combined into a kit that is pre-prepared for a given type of surgical procedure. The tip of the laser fiber of the invention can be formed at a predetermined length by which to ensure that it will remain viable for the duration of one or more types of endoscopic surgical procedures. The fiber with extended tip can then be pre-inserted into the self-aligning stability sheath with the extended tip safely withdrawn in side of the sheath. The kit is provided with a Tuohy-Borst adapter, through which the sheath and fiber are inserted. The Tuohy-Borst adapter can then be configured to seal the sheath around the fiber, thereby resisting movement of the fiber with the sheath to ensure the extended tip remains withdrawn therein until use.

The kit of the invention alleviates the need for medical personal to, just prior to initiating a procedure, form the extended tip to accommodate the burn-back of the particular procedure to be performed. It will further eliminate the use of an extended tip that will not have the benefit of an uncompromised polymeric coating due to the stripping process. It will further eliminate the need for the medical personnel to insert the fiber into the sheath, and to couple the Tuohy-Borst adapter for use during the procedure. Finally, the extended tip can remain safely retracted within the sheath until self-alignment of the sheath with the endoscope has been completed.

BRIEF DESCRIPTION OF THE DRAWINGS

FIG. 2 illustrates an extended tip of an embodiment of the laser fiber of the invention from its proximal to its distal ends;

FIG. 3A is a detailed illustration of the distal end of the extended tip of FIG.2;

FIG. 3B is a detailed illustration of the proximal end of the extended tip of FIG.2;

DETAILED DESCRIPTION

Figure 1:
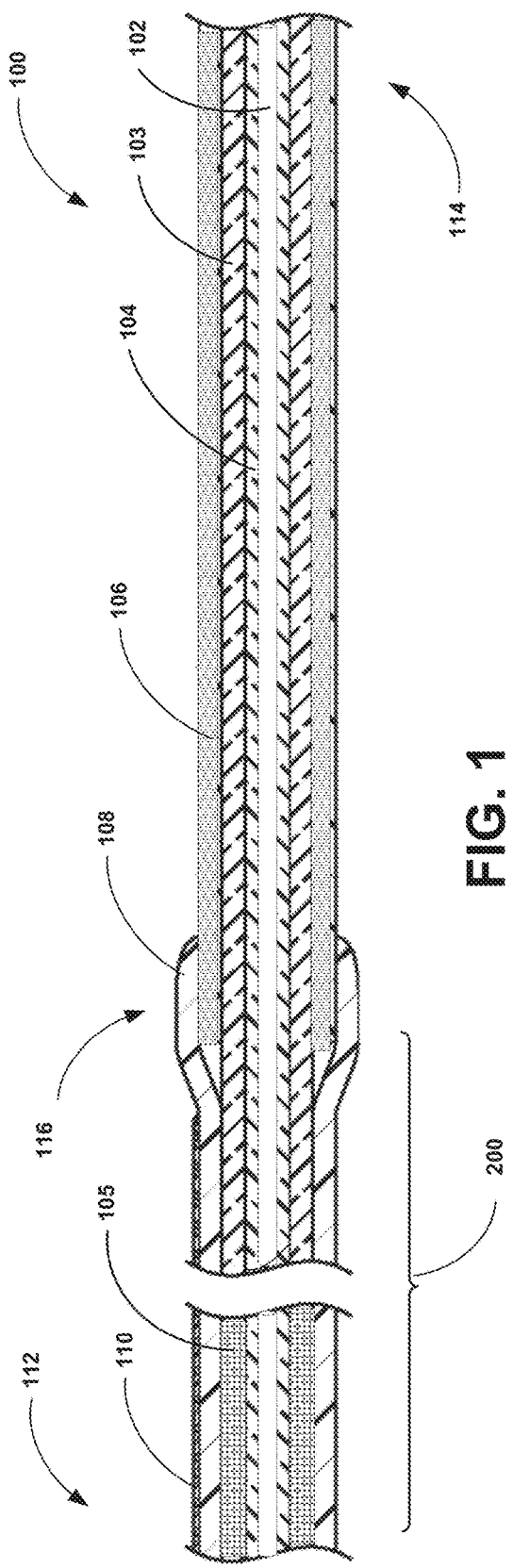
FIG. 1 is a cross-sectional view of the processed layers of an embodiment of a laser fiber of the invention having an extended tip from which the jacket has been stripped and then a new polymeric coating has been applied.

A laser fiber of the invention is provided to medical personnel in having an extended tip that is stripped of the jacket (and most if not all of the original polymeric coating), and is then coated with a second application of a polymeric coating to protect its cladding. The length of the extended tip is predetermined as suitable for one or more targeted types of endoscopic surgical procedures, the suitability based on variables such the typical expected burn-back rate of the targeted procedure(s) and the typical (or even maximum) expected duration of the targeted procedures. Thus, the predetermined length of the fiber can be chosen such that the extended tip will remain viable throughout the targeted procedure, thus eliminating interruptions and delays in the procedure.

The laser fiber of the invention also greatly reduces the likelihood that such a tip will be compromised through handling, eliminates the need for medical personnel to perform their own modifications to extend the tip prior to initiating procedures requiring longer tip lengths, as well the necessity for making such modifications when a tip completely burns back to the jacket of the fiber prior to completion of the procedure. When such modifications are required of medical personnel, delays and interruptions to procedures, as well as waste lead generally to increased costs and lost time.

Additionally, the laser fiber of the invention solves a problem associated with extended fiber lengths. Namely, visually ascertaining the spatial location of the distal end of an elongated tip while targeting objects in the surgical field. This is made difficult because the tip is largely clear. When conventionally shorter tips are used, the proximal end of the tip, which is defined by the boundary of the jacket layer on the fiber and which defines the proximal end of the tip, provides a visible indication by which the spatial location of the distal end of the tip may be gauged. Elongated tips lead to the jacket boundary not being visible until burn-back has sufficiently shortened the tip to a length very similar to conventional tip lengths.

Applicant's laser fiber of the invention provides a visual indicator that can be pad printed right onto the tip. The second layer of the polymeric coating permits this application, which would not be possible if the tip is merely stripped of its jacket just prior to, or in the middle of, a procedure.

In addition, certain laser fibers are employed in endoscopes that do not have a lumen though which the fiber is supported during its use. Endoscopes such as cystoscopes only have ring feature at the very end of the scope through which a fiber is aligned as it exits the distal end of the scope. Thus, the fiber is first inserted into a stability sheath before insertion into the cystoscope. Manual alignment is difficult because the ring feature is not readily viewed during insertion. Thus, Applicant's self-aligning stability sheath allows for easier insertion prior to use of the laser fiber of the invention.

Finally, Applicant discloses a laser fiber kit of the invention, that combines the laser fiber of the invention with an extended tip of predetermined length suitable for targeted endoscopic procedures, pre-inserted into Applicant's self-aligning stability sheath. The fiber is packaged with the extended tip withdrawn inside of the sheath, and a Tuohy-Borst adapted is provided by which to restrain the fiber from moving in relation to the sheath. Thus, medical facilities and professionals will be able to purchase a laser fiber that already has an extended tip that is suitable for the procedure(s) which they intend to perform, having a tip length that will ensure a viable tip for the entire procedure, and that is already inserted into a self-aligning and is ready to simply be inserted into an endoscope for performing the procedure. Moreover, the laser fiber is packed safely within the stability sheath until it is ready for use, with no delays for prepping the fiber for the particular procedure, no need for personnel to handle the fiber and risk damaging it, and there are no delays to initiating the procedure, or interruptions once initiated until the procedure is completed.

Those of skill in the art will recognize that there are many sources and types of laser fibers available, with their various specifications being dictated by typical variables such as intended application. Those of skill in the art will appreciate that Applicant's invention as disclosed herein is applicable to a wide range of such fibers and should therefore not be limited to in scope to the exemplary embodiments disclosed herein.

FIG. 1 shows a cross-sectional view of an embodiment 100 of a laser fiber of the invention. The laser fiber 100 includes an elongate silica core 102 surrounded by a silica cladding 104. The proximal region 114 of the fiber includes an original layer of a polymeric coating 103 to protect the cladding 104, and the original coating 103 is protected by a surrounding fluoropolymer jacket 106. The proximal region 114 of the optical fiber terminates in a connector (not shown) that couples to a laser. One example connector that can be used in this regard is a SMA-905-style connector used in conjunction with a strain relief connector and a dust cover.

The distal region of the fiber includes a tip 200 of a predetermined length. The extended tip 200 is formed by stripping off the of the fluoropolymer jacket 106 over the length of the extended tip 200. The original polymeric coating 103 is also mostly if not completely stripped along with jacket 106, and is at the very least severely compromised as indicated by layer 105. Once the fluoropolymer jacket 106 is removed, the exposed fiber is coated with a second layer of protective polymeric coating 108. This can be of the same composition as the original coating 103, or it can be different but suitable composition.

The silica core 102, silica cladding 104, the polymeric coatings 103 and 105, and fluoropolymer jacket 106, all have respective refractive indices which are selected for the transmission of light generated by a laser light source, as will be discussed in turn below.

In various embodiments, the silica core 102 can have a diameter of between about 365 μm and about 800 μm, about 550 μm±100 μm, about 550 μm±50 μm, or about 550 μmm. The silica core 102 has a length that is appropriate for the particular medical treatment being undertaken. For example, in various embodiments adapted for the treatment of benign prostatic hyperplasia (BPH), the silica core has a length of about 2.5 m±1.0 m, about 2.5 m±0.5 m, about 2.5 m±0.2 m, or about 2.5 m. While the core 102 of the optical fiber comprises silica in one embodiment, other materials appropriate for transmitting light generated by, for example, a holmium yttrium aluminum garnet (Ho:YAG) laser or a thulium laser can be used as well. In an embodiment, the core of the optical fiber is capable of use with a 100 Watt Ho:YAG laser.

In another embodiment, the silica core 102 has a substantially constant diameter extending from a proximal region to a distal region. In an alternate embodiment, the distal region 112 of the silica core 102, or the distal end (220, FIGS. 2, 4) of the silica core 102, has a larger diameter than other regions of the core. This can be accomplished by fusing a relatively larger diameter silica core to the relatively smaller diameter silica core.

In various embodiments, the larger diameter silica core 102 that forms the distal region 114 of the silica core has a diameter that is between about 600 μm and about 1400 μm, between about 800 μm and about 1200 μm between about 950 μm and about 1050 μm or about 1000 μm. The two segments can be fused end-to-end to form a unitary optical fiber. This two-segment fiber configuration results in slower fiber degradation, also referred to as "burn-back" that occurs when the distal end of the extended tip 200 of the optical fiber 100 melts or is otherwise destroyed during operation of the laser. In particular, distributing the optical energy over a larger cross-sectional area fiber in the distal region 114 causes less damage to the fiber as compared to when the same amount of energy is distributed across a smaller cross-sectional area. In still other embodiments, more than two different segments of varying fiber diameter can be implemented.

In an embodiment, the fluoropolymer jacket 106 comprises ethylene tetrafluoroethylene (ETFE), although other similar materials can be used in other embodiments. The fluoropolymer jacket 106 protects the silica core 102 from damage and deterioration caused by exposure to moisture or other harmful substances. In one implementation, the fluoropolymer jacket 106 has an outer diameter of about 750

μm±100 μm, about 750 μm±50 μm, about 750 μm±30 μm, or about 750 μm. In manufacturing, the fluoropolymer jacket 106 initially extends the entire length of the silica core 102, but a distal portion 114 is subsequently removed to form the tip 200 as illustrated in FIG. 1. In various embodiments of the invention, the fluoropolymer jacket 106 is removed from a predetermined length of the distal region 114 (starting at the distal end 220, FIGS. 2 and 4) as shown, and the resulting tip 200 can have a length of between about 2 cm and about 15 cm, about 10 cm±5 cm, about 10 cm±2 cm, about 10 cm±1 cm, or about 10 cm.

In one embodiment, once the fluoropolymer jacket 106 is removed, the exposed portion of the fiber 100 defining the extended tip 200 is dip-coated with a second layer of polymeric coating 108, such as acrylate or polyimide. In such embodiments, the second polymeric coating 108 covers that portion of the fiber from which the fluoropolymer jacket 106 was removed, thus providing the resulting extended tip 200 with a degree of protection from physical or chemical damage. The second polymeric coating 108 optionally extends over the distal portion defining the boundary of the remaining fluoropolymer jacket 106 in an overlap region 116. In various embodiments, the second polymeric coating 108 has a thickness between about 0.0001 inches and about 0.005 inches, between about 0.0005 inches and about 0.003 inches, or between about 0.0010 inches and about 0.0025 inches.

Figure 4:
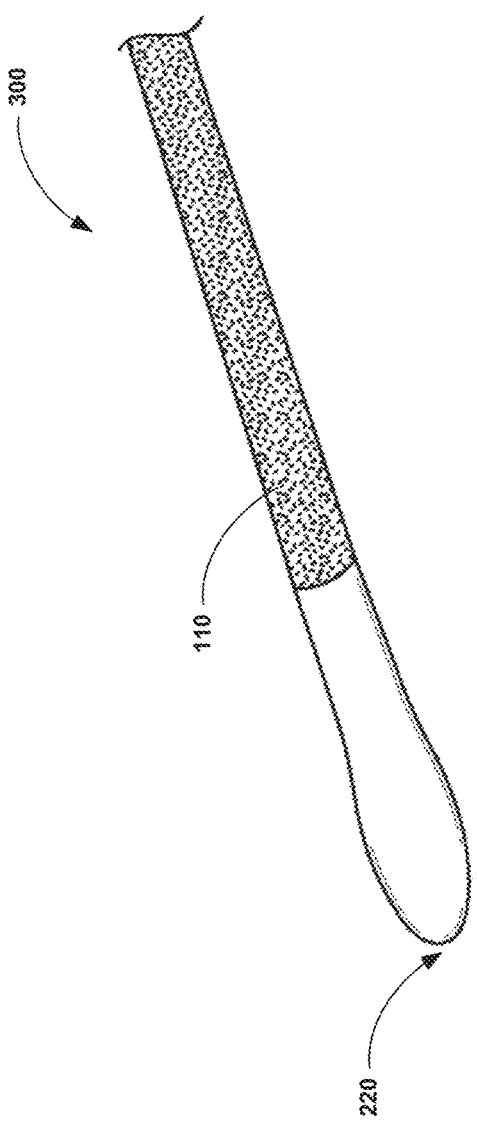
FIG. 4 is a detailed illustration of the printed visual indicator at the distal end of the extended tip of FIG. 2.

In an embodiment, the second polymeric coating 108 optionally includes a visual reference indicator 110 in the form of a printed line. As previously discussed, this visual indicator 110 makes it easier to see the distal end (220, FIGS. 2 and 4) of the fiber 100 when viewed using optics associated with the endoscope. The printed line 110 can have any orientation along the second polymeric coating 108, including, for example, either a straight line, a spiral line wrapped around the fiber 100, or any other suitable orientation that is visible when the fiber 100 is visible when an operator is using optics associated with the endoscope in which the fiber 100 is being used. In various embodiments, a distal end of the printed line 110 terminates within about 2.0 mm±1.5 mm, about 2.0 mm±1.0 mm, about 2.0 mm±0.5 mm, or about 2.0 mm from the distal end of the optical fiber. In various embodiments, the printed line has a length of about 10 cm±1 cm, about 10 cm±0.5 cm, about 10 cm±0.1 cm, or about 10 cm. FIG. 4 illustrates a magnified view of the relationship 300 between the visual indicator 110 and the distal end 220 of the tip 200.

FIG. 2 illustrates an isolated view of the extended tip 200 of the invention. Detail 3A of the distal area 112 and distal end 250 are shown in FIG. 3A. Detail 3B of the proximal end 260 of the tip 200 is illustrated in FIG. 3B, showing the proximal end 260 of tip 200, as the tip ends at the overlap area 116. The printed visual indicator 110 is also illustrated in both FIG. 3A and FIG. 3B.

Figure 5:
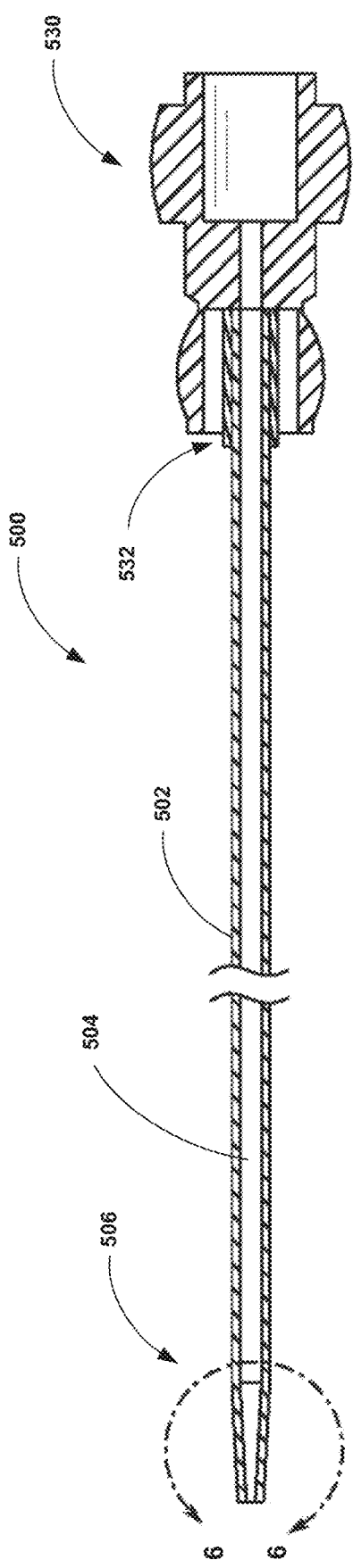
FIG. 5 is a cross-sectional view of an embodiment of the self-aligning stability sheath of the invention.

FIG. 5 is a cross-sectional view of the self-aligning stability sheath 500 of the invention. In an embodiment, the stability sheath 500 comprises an elongate hollow polyurethane tube 502 having an inner diameter and an outer diameter. The stability sheath 500 has a tapered distal end 506, where both the inner and outer diameters are reduced in a tapered fashion from the proximal to the distal end. This tapered end 506 allows the stability sheath to easily engage with a corresponding feature (808, FIG. 7) located in the distal region of an endoscope. The outer diameter of the stability sheath 500 is slightly larger than the inner diameter of the feature (808, FIG. 7), thus making it easy to hold the distal region of the stability sheath in alignment with respect to the endoscope.

Figure 6:
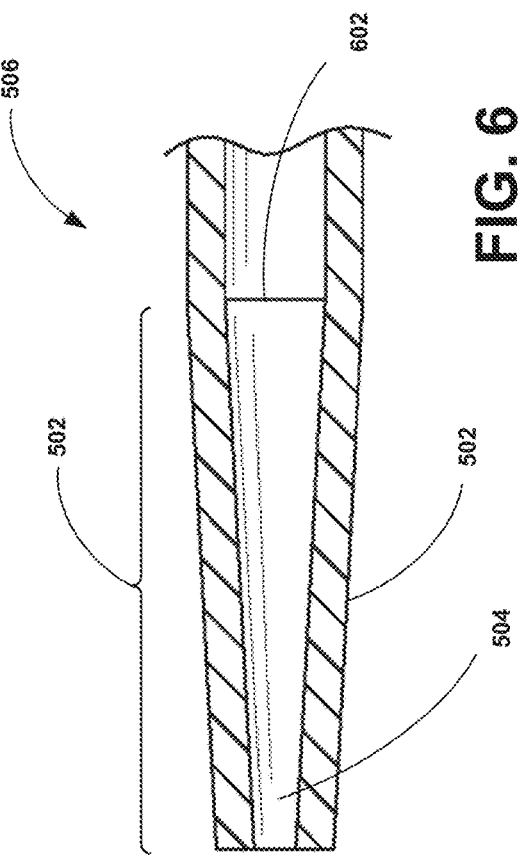
FIG. 6 is a detailed cross-sectional view of the distal end of self-aligning stability sheath of the invention as shown in FIG. 5.

FIG. 6 shows in detail the tapered portion 502, starting at 602, of the distal end 506 of the stability sheath of the invention 500. The interior diameter of the tapered region 506 is large enough to allow the optical fiber (not shown), which is inserted into and passes through the internal diameter 504, to pass therethrough. A Tuohy-Borst adapter 530 is mounted to a proximal region of the stability sheath. Once the optical fiber is inserted through the interior diameter 504 of the stability sheath, actuating the Tuohy-Borst adapter 530 will close seal mechanism 532, which can be used to resist movement of the optical fiber (100, FIG. 1) relative to the sheath 500. Cyclohexanone can be used to bond the Tuohy-Borst adapter 530 to the stability sheath 500.

In various embodiments, the stability sheath 500 can have an outer diameter between about 5 French and about 10 French, of about 9 French±5 French, about 9 French±3 French, about 9 French±1 French, or about 9 French. In various embodiments, the stability sheath 500 can have a length of about 33 cm±5 cm, about 33 cm±2 cm, about 33 cm±0.5 cm, or about 33 cm. In various embodiments, the hardness of the stability sheath 500 can be between about 30 shore D and about 120 short D, between about 60 shore D and about 90 shore D, or between about 75 shore D and about 85 shore D. Those of skill in the art that other dimensions and tolerances may be implemented to accommodate different endoscopes and laser fibers.

In one embodiment the stability sheath 500 is comprised of polyurethane, although other similar materials can be used in other embodiments. In other embodiments the stability sheath can be substantially transparent, which improves visualization of the optical fiber within the stability sheath 500. In addition, a transparent sheath 500 can be desirable to aid in determining the integrity of the optical laser fiber disposed therein. If the operator turns on a red or green aiming beam typically provided with many endoscopes, if the laser fiber has been damaged, it will not transmit the light from the aiming beam. Thus, an operator can easily confirm the integrity of the laser fiber when the light from the beam can be observed to be glowing through the sheath 500.

Figure 7:
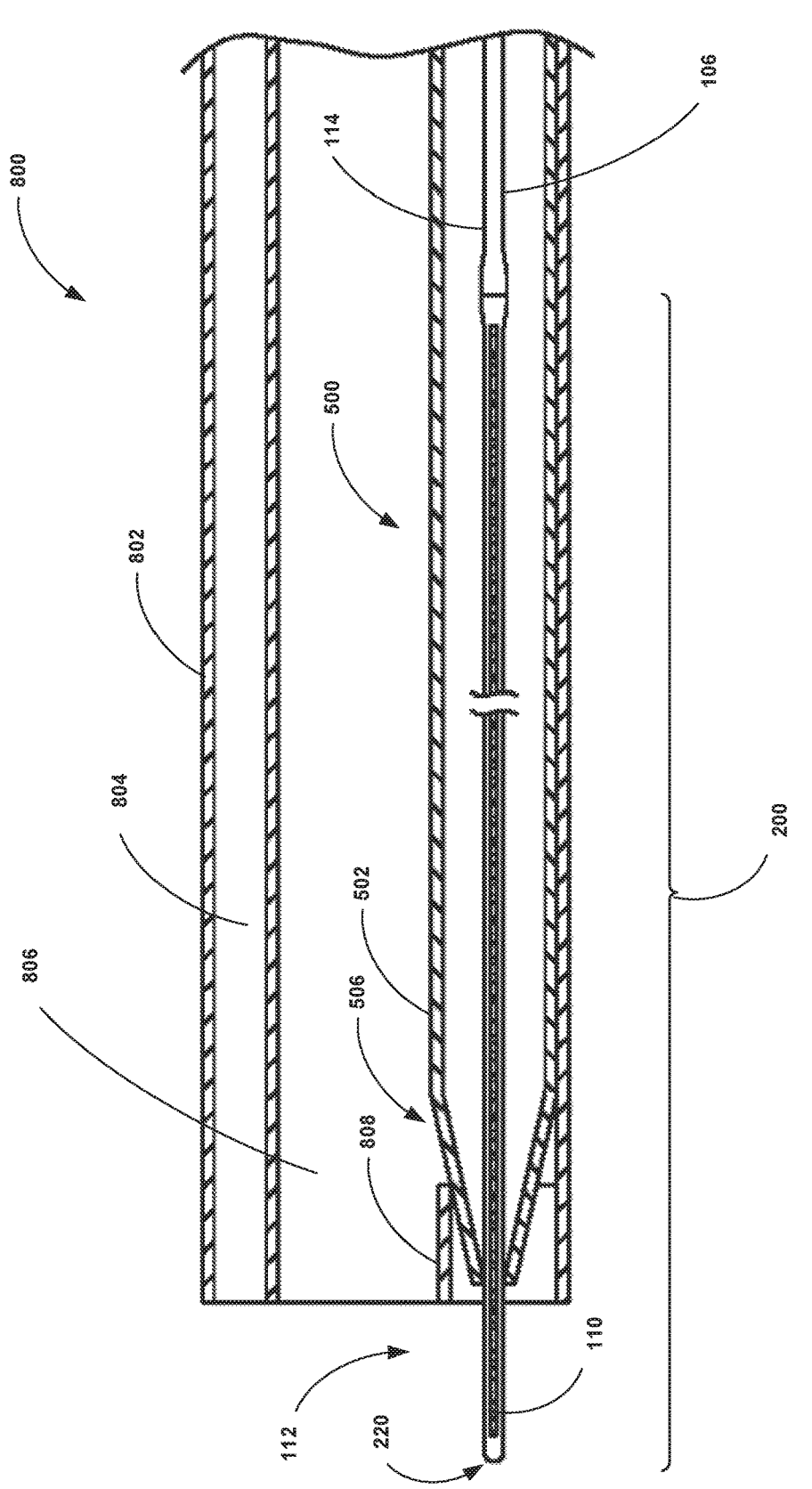
FIG. 7 is a cross-sectional view of an embodiment of the laser fiber of the invention inserted into an embodiment of the self-aligning stability sheath of the invention, and both inserted into and self-aligned with an endoscope.

FIG. 7 is a cross-section 800 of an endoscope 802, through which the laser fiber of the invention 100 is inserted into self-aligning stability sheath 500, which is in turn inserted into the cannula 806 of the endoscope 802. Distal end 506 of sheath 500 is inserted within alignment feature 808 until the outer diameter of tube 502 has exceeded the inner diameter of feature 808. Feature 808 can be a short tube, a ring or any other structure providing a geometry that permits insertion of distal end of 506 of sheath 500 until its further movement forward is restricted in a self-aligned position. The sheath 500 now remains aligned with only a slight forward force from the operator to hold it in place.

Once the sheath is aligned, distal end 220 of tip 200 can be advanced forward from the sheath 500 to target tissue or other objects in the surgical view, provided by an optics assembly typically inserted into channel 804. The tip 200 has been extended to a length that is predetermined to be long enough to remain viable throughout the procedure to be performed, notwithstanding the burn-back that will occur during the procedure. The printed visual indicator 110 will aid the operator in gauging how far outside of the scope 802 the distal end of the tip is extended toward the surgical targets to be treated.

Figure 8:
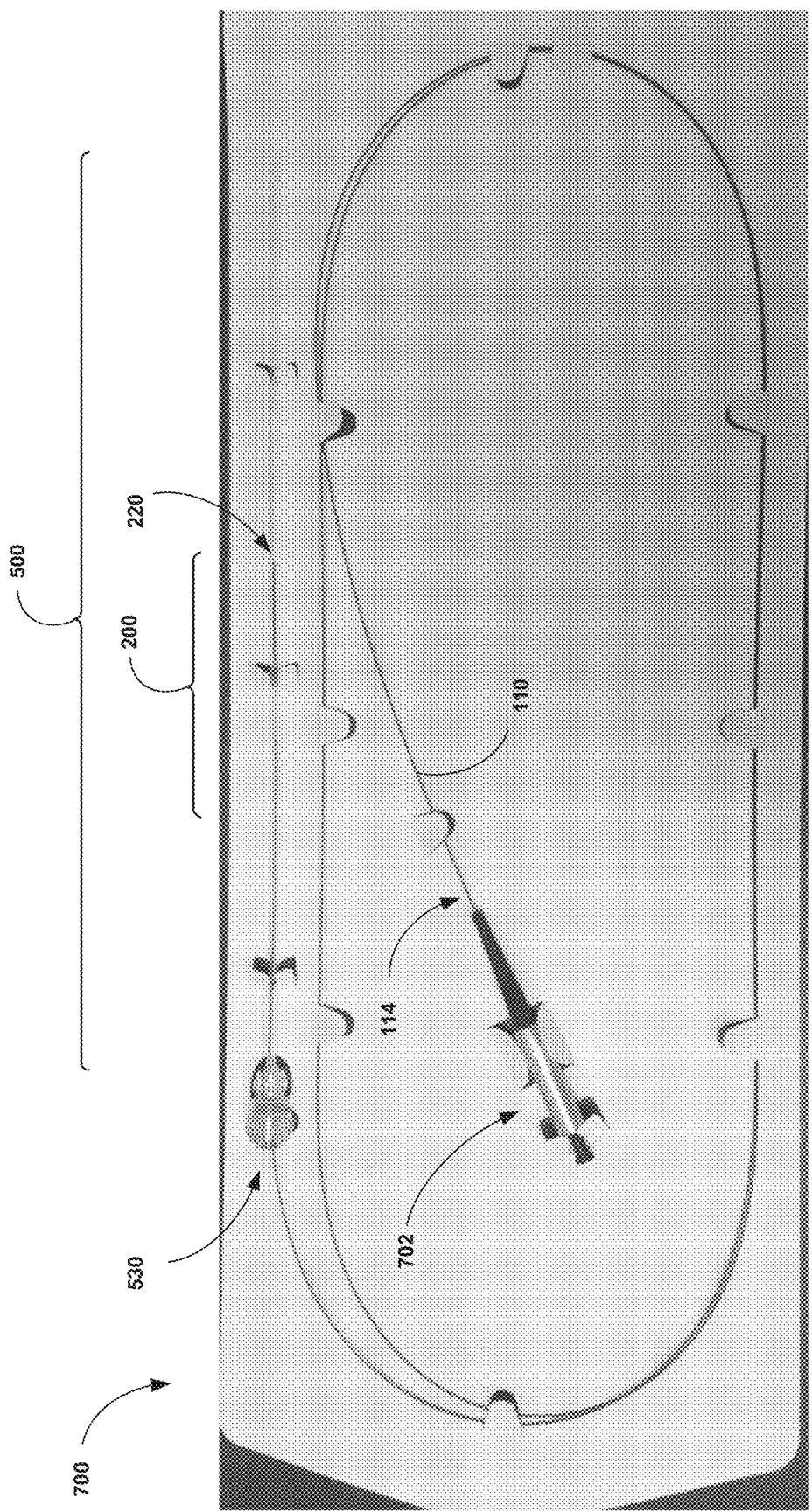
FIG. 8 is a plan view of a "ready-for-use" laser fiber kit of the invention, which includes a laser fiber of the invention, having an extended tip sized for one or more predetermined surgical procedures, pre-inserted into a self-aligning stability sheath of the invention and secured therein with a Tuohy-Borst adapter.

FIG. 8 illustrates an embodiment of a laser fiber kit 700 of the invention. The kit 800 includes an appropriately sized laser fiber 100 that is suitable for at least one targeted endoscopic surgical treatment. In addition, a properly coated extended tip 200 has been formed with a length that has been pre-determined to be of sufficient length that the tip 200 will remain viable throughout the duration of the targeted procedure/treatment notwithstanding the expected amount of burn-back. The laser fiber 100 is pre-inserted into an appropriately sized self-aligning stability sheath 500 of the invention. The tip 200 is completely withdrawn inside of the sheath 500 for added protection. A Tuohy-Borst adapter 530 is included and coupled to the proximal end of the stability sheath 500. The adapter 530 is actuated to hold the laser fiber 100 within the sheath until a user is ready to use it for a targeted procedure. An adapter 720 is coupled to the proximal end 114 of the fiber 100, the adapter being suitable to couple a laser, that is of a kind used in the targeted procedure, to the fiber 100.

Figure 9:
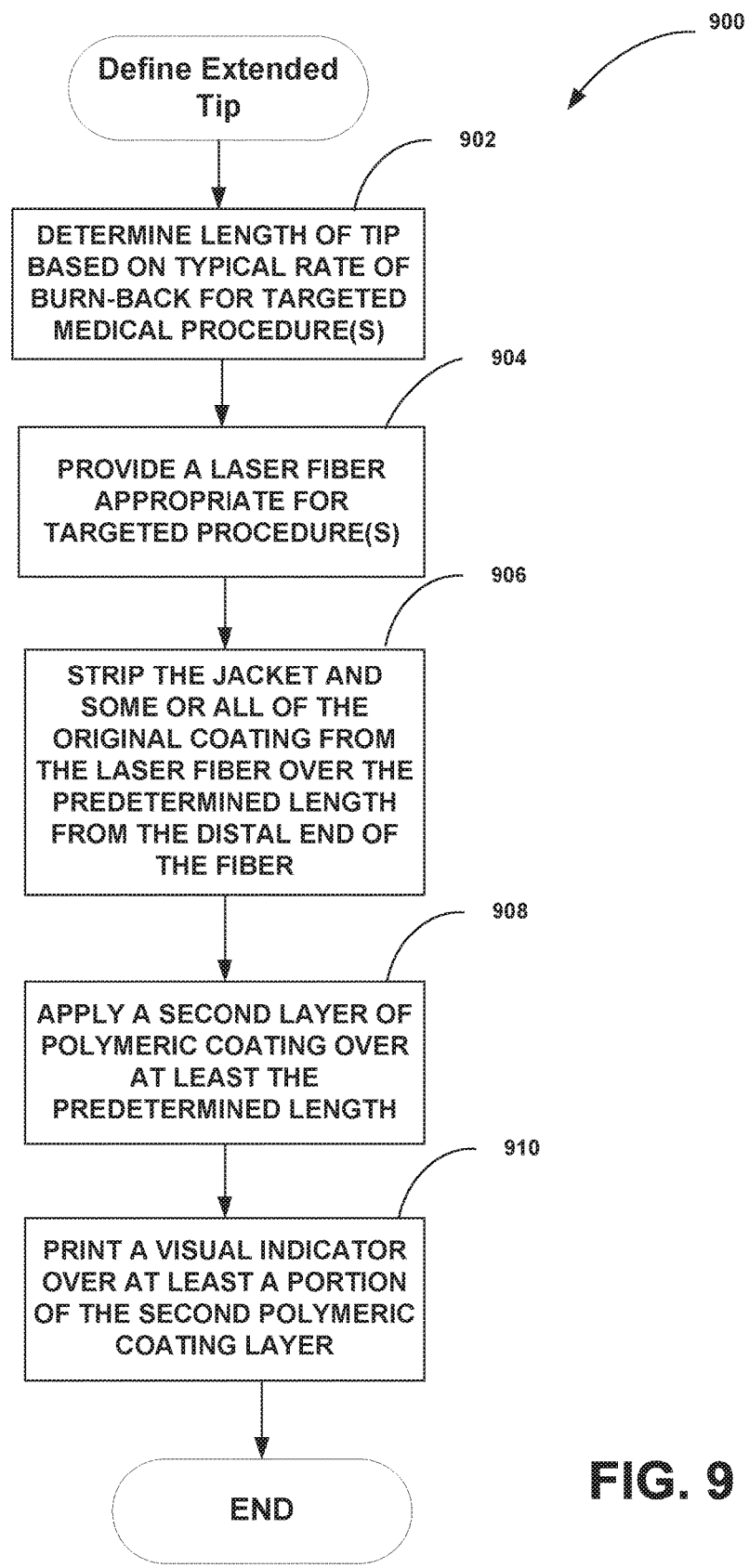
FIG. 9 is a procedural flow diagram illustrating an embodiment of a method of manufacturing the laser fiber of the invention

FIG. 9 illustrates a process 900 for manufacturing the laser fiber of the invention. The process includes the following steps that are specifically for creating the extended tip 200. At 902, determine the appropriate length of the extended tip based on typical rate of burn-back for targeted medical procedure(s). At 904, provide a laser fiber appropriate for application to the targeted procedure(s). At 906, strip the jacket and some or all of the original polymeric coating from the laser fiber over the predetermined length from the distal end of the fiber. At 908, apply a second layer of polymeric coating over at least the predetermined length. In some embodiments, at 910, print a visual indicator over at least a portion of the second polymeric coating layer.

What is claimed is:

1. A laser fiber for delivering laser energy to a surgical field continuously for the duration of at least one type of endoscopic surgical procedure, said laser fiber comprising:
    an elongate silica core having a proximal and distal end, the proximal end configured to be coupled to a laser;
    a layer of silica cladding material surrounding the core;
    an original layer of polymeric coating surrounding the silica cladding; and
    a fluoropolymer jacket surrounding the polymeric coating, and
    a tip extending from a distal end of the fiber and having a predetermined length, the tip defined by completely stripping the fluoropolymer jacket from the laser fiber over the length of the tip, and applying a second polymeric coating over at least the length of the tip, the second polymeric coating at least partially overlapping the fluoropolymer jacket, the predetermined length ensuring that at least a portion of the tip will remain continuously viable, notwithstanding burn-back of the tip, throughout the at least one type of surgical procedure.

2. The laser fiber of claim 1, wherein a visual indicator is printed over the length of the tip.

3. The laser fiber of claim 1, wherein at least the second polymeric coating is an acrylate.

4. The laser fiber of claim 1, wherein the predetermined length is at least one centimeter.

5. The laser fiber of claim 1, wherein the fluoropolymer jacket material is tetrafluoroethylene (ETFE).

6. The laser fiber of claim 1, wherein the length of the tip is between about 1 centimeter and about 15 centimeters.

7. A laser fiber for delivering laser energy to a surgical field continuously for the duration of at least one type of endoscopic surgical procedure, said laser fiber prepared by a process comprising:
    providing a laser fiber including:
        an elongate silica core having a proximal and distal end, the proximal end configured to be coupled to a laser;
        a layer of silica cladding material surrounding the core;
        an original layer of polymeric coating surrounding the silica cladding; and
        a fluoropolymer jacket surrounding the polymeric coating;
    forming a tip extending from the distal end of the laser fiber for a predetermined length, said forming further comprising:
        stripping the fluoropolymer jacket completely from the laser fiber over the length of the tip; and
        applying a second polymeric coating over at least the length of the tip, the second polymeric coating applied by dipping the laser fiber past the tip portion to form an overlap portion where the second polymeric coating overlaps the fluoropolymer jacket,
        wherein the predetermined length ensures that at least a portion of the tip will remain continuously viable, notwithstanding burn-back of the tip, throughout the at least one type of surgical procedure.

8. The laser fiber of claim 7, wherein said process further comprises applying a visual indicator over at least a portion of the length of the tip.

9. The laser fiber of claim 8, wherein said applying further includes pad printing the visual indicator to the second polymeric coating.

10. The laser fiber of claim 7, wherein said second polymeric coating is applied by dipping at least the tip portion of the laser fiber into the polymeric coating.

11. The laser fiber of claim 7, wherein at least the second polymeric coating is an acrylate.

12. The laser fiber of claim 7, wherein the predetermined length of the tip ranges between about 1 centimeter and about 15 centimeters.

13. A laser fiber assembly for delivering laser energy to a surgical field through an endoscope comprising: a laser fiber including: an elongate silica core having a proximal and distal end, the proximal end configured to be coupled to a laser; a layer of silica cladding material surrounding the core; an original layer of polymeric coating surrounding the silica cladding; and a fluoropolymer jacket surrounding the polymeric coating, and a tip extending from a distal end of the fiber and having a predetermined length, the tip defined by completely stripping the fluoropolymer jacket from the laser fiber over the length of the tip, and applying a second polymeric coating over at least the length of the tip, the second polymeric coating extending past the tip portion to form an overlapping portion where the second polymeric coating overlaps the fluoropolymer jacket, the predetermined length ensuring that at least a portion of the tip will remain continuously viable, notwithstanding burn-back of the tip, throughout the at least one type of surgical procedure; a stability sheath including: an elongate hollow polyurethane tube having an inner diameter and an outer diameter, wherein the inner diameter of the tube is large enough to permit the laser fiber to pass therethrough, and the inner and outer diameters of the tube decreasing to form a taper at distal end of the tube; and wherein the distal end of the laser fiber is configured to be inserted into the proximate end of the stability sheath, and the proximate end is configured to receive a Tuohy-Borst adapter, whereby when the assembly is inserted into a proximate end of the endoscope, the tapered distal end of the stability sheath is configured to be received by a ring feature disposed at a distal end of the endoscope, the ring feature having a diameter that is at least less than the outer diameter of the non-tapered portion of the stability sheath such that the tapered distal end of the stability sheath will engage with, but not pass entirely through, the ring feature, thereby self-aligning the sheath with the end of the endoscope.

14. The laser fiber assembly of claim 13, wherein the Tuohy-Borst adapter is configured to resist movement of the laser fiber within the stability sheath.

15. The laser fiber assembly of claim 13, wherein the stability sheath is made of polyurethane.

16. The laser fiber assembly of claim 13, wherein the tip of the laser fiber includes a visual indicator printed over at least a portion of the length of the tip.

17. The laser fiber assembly of claim 13, wherein the predetermined length of the tip ranges between about 2 centimeters and about 15 centimeters.

* * * * *